(12) United States Patent
Shteyn

(10) Patent No.: US 7,403,693 B2
(45) Date of Patent: Jul. 22, 2008

(54) PVR SET-UP OVER THE INTERNET

(75) Inventor: Yevgeniy Eugene Shteyn, Cupertino, CA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 1295 days.

(21) Appl. No.: 10/606,337

(22) Filed: Jun. 25, 2003

(65) Prior Publication Data

US 2004/0060071 A1 Mar. 25, 2004

Related U.S. Application Data

(63) Continuation of application No. 09/283,545, filed on Apr. 1, 1999, now Pat. No. 6,040,301.

(51) Int. Cl.
*H04N 7/00* (2006.01)
*H04N 5/91* (2006.01)
*H04N 7/173* (2006.01)

(52) U.S. Cl. ............... 386/83; 386/46; 725/86
(58) Field of Classification Search ............... 386/83, 386/46, 69, 68, 1, 95, 4, 52, 55; 725/86, 725/87, 88, 101, 102, 103
See application file for complete search history.

(56) References Cited

U.S. PATENT DOCUMENTS

| 4,977,455 | A | * | 12/1990 | Young | 348/460 |
| 5,270,829 | A | * | 12/1993 | Yang | 386/83 |
| 5,541,738 | A | * | 7/1996 | Mankovitz | 386/83 |
| 5,589,945 | A | * | 12/1996 | Abecassis | 386/83 |

* cited by examiner

*Primary Examiner*—Robert Chevalier

(57) ABSTRACT

A server system enables a subscriber to select a specific broadcast program for recording and a specific location and time frame for play-out of the recorded program.

8 Claims, 2 Drawing Sheets

PVR SET-UP OVER THE INTERNET

Figure 1:
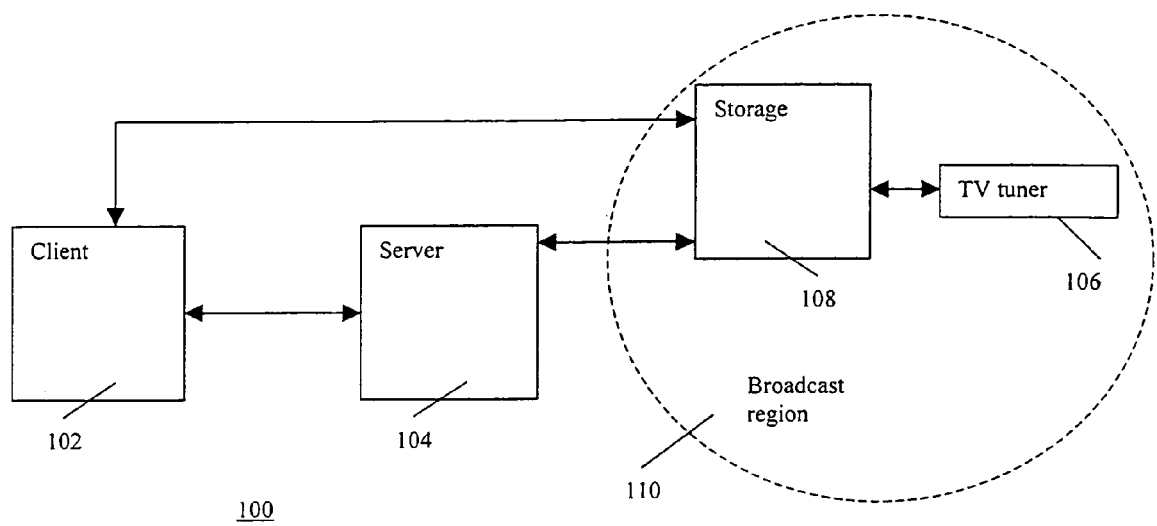
Figure 2:
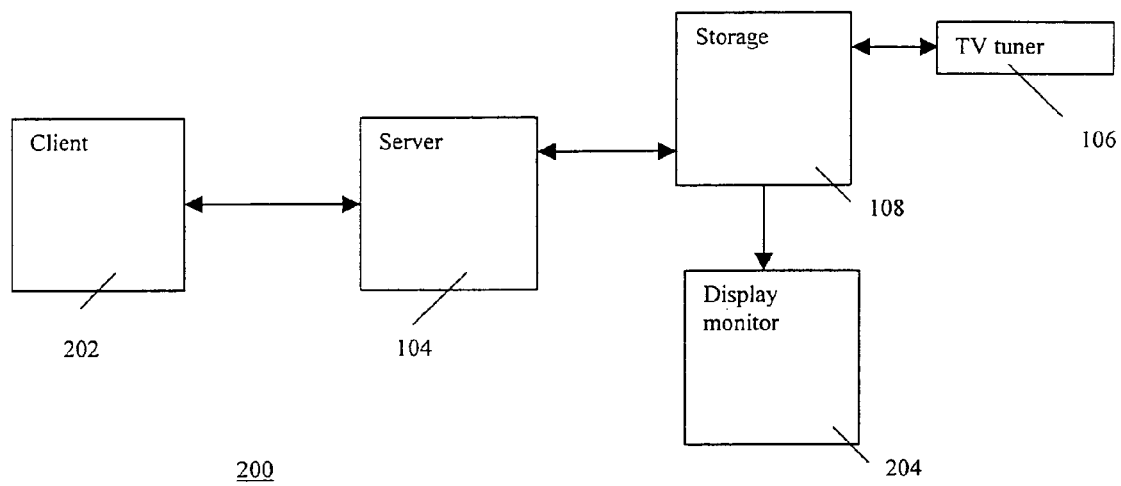

This is a continuation of US patent application of the same assignee Ser. No. 09/283,945 filed Apr. 1, 1999, now U.S. Pat. No. 6,040,301.

The invention relates to a system and method for providing information content to an end user.

Several companies, e.g., TiVo, Inc., have been developing recording devices that enable to time-shift (pause, rewind, and slow-motion) play-out of live TV broadcasts. The user has to subscribe to a service (provided via a modem), and to connect the device between a TV, and a satellite receiver, cable box or antenna. The service provides an electronic program guide (EPG) based on the user-profile that develops over time. The service learns from the user what he or she prefers and will automatically record favorite shows and make suggestions about other shows based on the user's preference profile.

The inventor has realized that it is a disadvantage that the service is location-specific. That is, mobile users cannot chose desirable programming from, and for, multiple geographically different places along their itinerary. It is therefore an object of the invention to broaden the scope of the known systems and services to provide more degrees of freedom to the end user.

To this end, the invention provides a method of enabling a user to access content information (e.g., video, audio). The method enables the user to select the content information, e.g., from an electronic program guide relating to a broadcast or multicast service. The selected content information gets recorded when it is broadcasted or multicasted. The method enables the user to select in advance at least a specific one from multiple geographically different locations at which the recorded, selected content information will be made available for play-out. Preferably, the invention also enables the user to specify a time frame for making the recorded content information available for play-out at the specific location. The content information can be recorded at a first recording system, e.g., at a server, whereafter the recorded selected content information is streamed over a data network, e.g., over the Internet or a private network like AOL, from the first recording system to the location specified by the user. If the specific location. has a second recording system, the streaming uses a low-bandwidth protocol so as to keep Internet bandwidth usage low while recording at the second recording system.

The invention lets the user specify in advance a location for play-out of a specific broadcast or multicast program pre-recorded in response to the user's selection, and has the content made available to him or her at that location. For example, the user can specify that he or she will be, e.g., at the house of a relative, at a specific hotel, on a particular flight of a specific airline, in a specific bar, a particular restaurant, etc., at a specific time period, and request that the content be recorded at this location. This requires that these other locations be integrated in the infrastructure of the service mentioned above.

The programs of a TV broadcasts are typically regional or local. If the user is traveling outside the region or the time zone, he or she may request to search for an identical program broadcasted in the new region, or a program of a similar content, or a program with identical or similar content but closer in time to the intended play-out, and record that program at a recording device in the pre-specified location.

Alternatively, or subsidiarily, a program can be recorded and stored temporarily at a server and then streamed over a data network, e.g., the Internet, using a low-bandwidth protocol, to a recording device specified by the user as destination. Note that bandwidth is not a critical factor in this service model or method of doing business, as recording and play-out occur as events separated in time.

The invention is based on an insight that several technological and demographic trends are emerging and gaining momentum: personalized information through Internet portals such as the web sites "my.yahoo.com", "my.excite.com", "cnn.com", etc. . . ; personalized TV such as provided by TiVo, Inc.; the availability of EPG's; home networking and home automation infrastructures, e.g., HAVi, Home API, JINI., tailored to the individual's equipment, preferences and needs; teleconferencing; and an increasing mobility of the individual: business travel and recreational travel, and as a consequence thereof, an increasing demand for high quality services. Accordingly, the invention attempts to contribute to the user's needs by means of enabling shifting of recording and play-out locations, in addition to the time-shifting provided by the known services.

The invention is explained by way of example and with reference to the accompanying drawings, wherein:

FIGS. 1-4 are block diagrams illustrating the method of the invention.

Throughout the figures, same reference numerals indicate similar or corresponding features.

Several scenarios are described below that illustrate attractive opportunities of exploiting the invention, with benefits to the end-user as well as to the service provider and content provider.

Travel services: Eugene is scheduled for an intercontinental business trip starting on a Sunday. An ice hockey game is broadcasted on Sunday by his local TV station at home. Eugene makes his reservations with a hotel that provides a program recording service. He specifies that he would like to watch the game in this hotel. FIG. 1 illustrates this process in a system 100 according to the invention. Client 102, here the hotel's system, forwards to a server system 104 a request to make available a recording of a certain broadcasted program. Server system 104 locates a tuner 106 and a storage system 108 within a region 110 wherein this particular program will be broadcasted. Upon having selected storage system 108, the latter is activated to record the program at the time of broadcast. Note that system 108 can be Eugene's own home recording system, as well as a storage system that belongs to a service provider in the particular region. During or upon recording, the recorded content is streamed over a data network, e.g., the Internet or over data networks as maintained by online services such as AOL or CompuServe, to hotel 102 using a low-bandwidth protocol. Hotel 102 records the content for scheduled play-out as desired by Eugene.

Assume that there are multiple broadcast regions available wherein the same program is scheduled for broadcast within a certain time frame. Then, server system 104 preferably selects storage system 108 in that particular region 110 wherein the broadcast takes place at a time that is most convenient in view of the duration contemplated for storing the content at system 108 and at client 102 and in view of the time it takes to stream the content over the Internet. By minimizing the occupancy time at system 108 and at client 102, storage capacity usage is optimized towards being able to service a larger number end-users.

Preferably, confirmative communication protocols are used between client 102 and server 104 and between server 104 and storage system 108 in order to have confirmed that the various actions are being taken necessary to get the desired content to hotel 102 in time. For example, storage system 108 may be out of order or may have run out of memory space. In these cases, server 104 may activate another storage system or have the end-user notified of alternatives.

Similarly, flight reservations can be made together with a reservation for a personalized in-flight entertainment program tailored to the preferences of each passenger. Each passenger seat is provided with a play-out device for making available pre-recorded content, e.g., audio or video. Client 102, e.g., the airline operator, receives a request for a personalized entertainment program on a particular flight. The program is based on pre-recorded content as broadcasted by a specific TV channel. The operator forwards the request to server 104 that in turn finds appropriate region 110 with storage system 108. Upon or during recording a pre-selected program, the recorded content is supplied to client 102 for local recording and/or subsequent play-out during the flight. This could again be done via a low-bandwidth protocol, or via a dedicated interconnection that enables high-bandwidth downloading into client 102.

Figure 3:
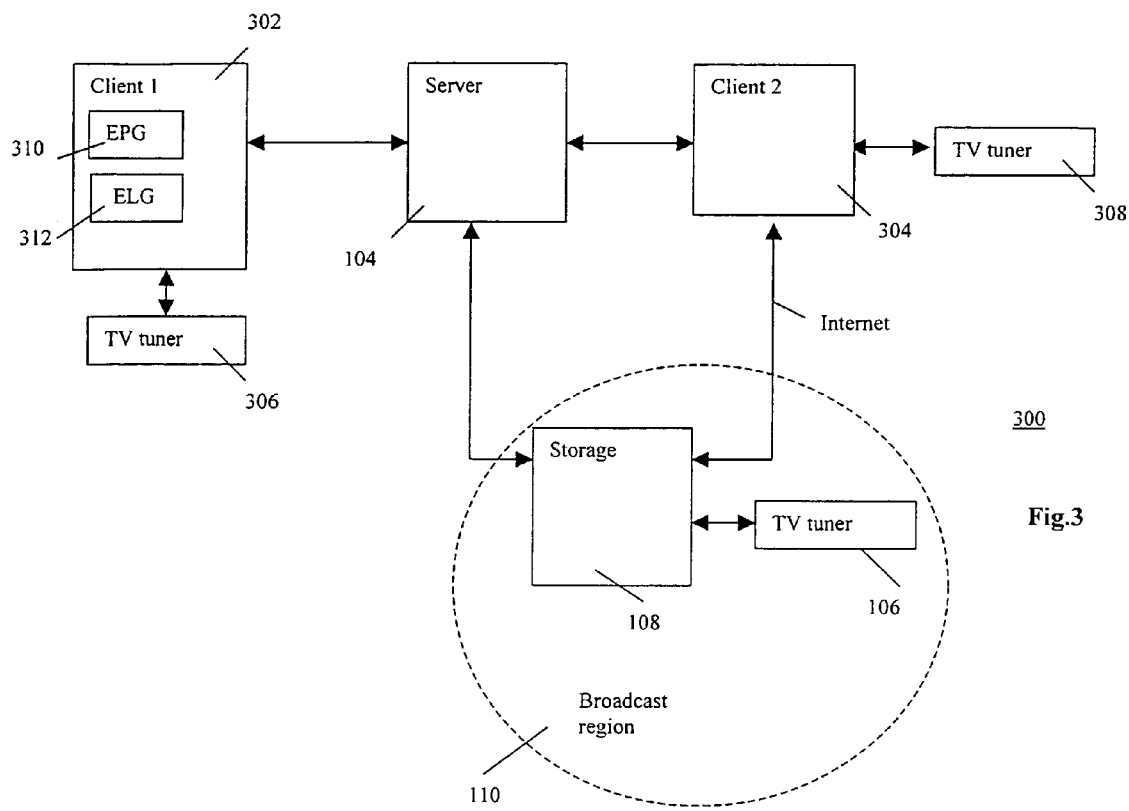

Ambient entertainment: Vladimir and his friends patronize a local sports bar establishment. They usually visit it on Fridays to relax after a long week at work. At the bar, they like to watch some basketball games together that were broadcasted in its entirety at the east coast earlier in the week. Vladimir and his friends, however, live on the west coast and saw only excerpts broadcasted by their local or regional TV station. FIG. 3 is a block diagram of a system 300 to illustrate how this can be achieved.

Vladimir and the sports bar proprietor have subscribed to a service provided by server 104. The service enables Vladimir and the proprietor to select broadcasts for being recorded at their own local client devices 302 and 304, respectively, and it enables Vladimir to record at the bar's client 304 with the authorization of the proprietor. Clients 302 and 304 are connected to local TV tuners 306 and 308, respectively, for recording local broadcasts. Each of clients 302 and 304 has a storage device (not shown), such as a hard disk, with a capacity large enough to store at least a few hours (play-out time) of video. Vladimir selects the desired program from an EPG 310 and the desired play-out location from an electronic location guide (ELG) 312. Both EPG 310 and ELG 312 are personalized services. In this case, the bar owner has authorized Vladimir to have bar's client 304 as a menu option in ELG 312. Vladimir therefore selects the broadcast of the basketball game for recording, and also the bar as location for play-out of the recorded basketball game. In addition, he specifies that he wants to have it available at the bar on Friday night later that week. Upon receiving this information from client 304, server 104 selects the appropriate region, here region 110, for locally recording the broadcast on storage system 108. After recording, the recorded content is supplied to client 304, e.g., via the Internet using a low-bandwidth protocol for local recording. Alternatively, if the desired broadcast takes place within the same region as that containing client 304, the recording of the content during the broadcast is made at client 304 directly without server storage 108 but under control of the server 104. In yet another scenario, server storage 108 is involved even if the broadcast takes place in the same region as wherein client 304 is located, for example, in order to relieve the local storage of client 304 that is typically more limited than that of server storage 108. Client 304 notifies server 104 of storage space available locally or already reserved for local recording, so that server storage 108 can serve as a temporary buffer. In yet another scenario, if there is sufficient bandwidth available, server storage 108 may stream the content directly to client 304 for playout, i.e., without local pre-recording at client 304.

Figure 4:
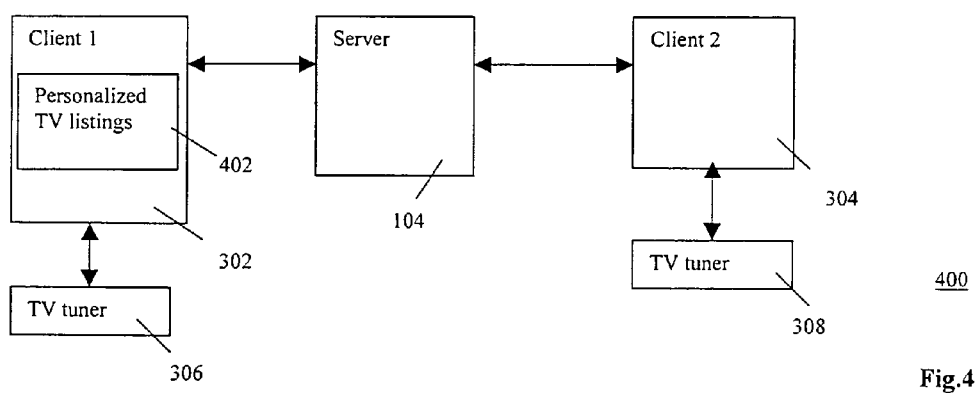

Web-based programming: FIG. 4 illustrates another scenario in a system 400. Svetlana accesses her personalized web page with TV listings 402 on her client 302. TV listings 402 are provided by services such as personalized information sites through Internet portals. She spots her favorite show, and decides to watch it later tonight. Svetlana remembers, however, that she has promised to visit her parents this evening. Instead of setting up the recording at her own client 402, she chooses to record the show on system 304 of her parents, so they can watch it together. She is authorized to make the reservation through server 108.

Examples of other scenarios illustrating the invention: Mobile user: Alice got stuck in traffic on her way home. She is going to be late for the broadcast of a live piano concert. Fortunately, her palm-top Nino (or cell phone, or laptop) can access the TV programming network. With just a couple of clicks Alice sets her recording time-shifting device to cache the concert. Enhanced Teleconference: Alice loves talking about her favorite TV series. She watches the episodes frequently and enjoys every minute of it. In today's episode one of the characters behaves exactly as she predicted a couple of days ago. Alice needs to talk to her friend Jane about it. Jane is at work and cannot see the show. Alice brings up her net menu and is authorized to select Jane's recording device. It has enough space reserved just for Alice. One click and today's phone discussion (teleconference) with Jane is going to be a real time experience. See within this context also: U.S. Ser. No. 09/053,448, filed Apr. 1, 1998 for Raoul Mallart and Atul Sinha for "Group-wise video conferencing uses 3D graphics model of broadcast event; and, U.S. Ser. No. 09/138, 782 filed Aug. 24, 1998 for Raoul Mallart and Atul Sinha for "Emulation of streaming over the Internet in a broadcast environment and U.S. Pat. No. 6,557,041, filed Sep. 9, 1998 for Raoul Mallart for "Real time video game uses emulation of streaming over the Internet in a broadcast environment", all incorporated herein by reference.

Above scenario's can be further enhanced by, e.g., having server 104 searching for a program identical to the one desired by the end-user but being broadcasted closer in time to the desired play-out time. This enables to reduce storage time at server storage 108. Alternatively, if the desired content is not available, the server may request the end-user to search for a program non-identical but of a similar type (e.g., western, football match, concert).

What is claimed is:

1. A method for making content available, the method comprising:
  enabling a user to access a server via a website over the Internet,
  receiving a user selection for a location;
  identifying a device at the location;
  receiving a selection by the user of a content item that will be broadcasted in the future;
  recording the content item in a storage memory and transferring the content item from the storage memory to the device at a time selected by the user.

2. The method of claim 1, wherein the transferring is a download of the content item from the storage memory to the device.

3. The method of claim 1, wherein the content item is streamed from the memory to the device upon request issued by the user at the device.

4. The method of claim 1, wherein the device is selected from a plurality of devices at the geographical location.

5. The method of claim 1, wherein the user selection for the location is a selection of one of a plurality of businesses or residents.

6. A method for enabling transfer of a television program, the method comprising:
- providing access to a server via a website over the Internet,
- enabling a user to identify a first device and a second device via the website being different from respective local user interfaces used to locally control the first and second devices;
- providing a list of content items stored at the first device;
- receiving a selection for one of the content items;
- enabling a conditional transfer of the content item from the first device to the second device upon connection of the second device to the server.

7. The method of claim 6, wherein the content item is transferred to the second device if a user of the second device has authorized the transfer.

8. The method of claim 6, wherein the content item is transferred from the first device to the second device if the second device has sufficient memory space to store the content item.

* * * * *